United States Patent [19]

Blake

[11] 4,326,952
[45] Apr. 27, 1982

[54] PRECIOUS METAL RECOVERY APPARATUS

[76] Inventor: Gene J. Blake, 635 S. Cleveland, Arlington Heights, Ill. 60005

[21] Appl. No.: 164,232

[22] Filed: Jun. 30, 1980

[51] Int. Cl.³ .............................................. B01D 21/08
[52] U.S. Cl. ..................................... 210/85; 210/243; 210/521; 210/532.1
[58] Field of Search .................. 210/94, 97, 232, 243, 210/521, 522, 532.1, 85; 433/92

[56] References Cited

U.S. PATENT DOCUMENTS

| | | | |
|---|---|---|---|
| 2,478,934 | 8/1949 | Morse | 210/243 |
| 3,272,343 | 9/1966 | Caldwell | 210/521 |
| 3,777,403 | 12/1973 | Ritchie | 433/92 |
| 3,912,533 | 10/1975 | Heyer | 210/521 |
| 4,058,897 | 11/1977 | Edwards | 210/522 |

*Primary Examiner*—Ivars C. Cintins
*Attorney, Agent, or Firm*—Alter and Weiss

[57] ABSTRACT

An apparatus for recovering precious metal particles from a liquid mixture environment, wherein liquid mixture containing varying sizes of valuable metal particulate is directed into a plurality of baffled compartments successively arranged in a sealed chamber. Elements within the compartments, together with additional jogging and skimming devices, segregate out the precious metal particles from the liquid mixture to release the liquid portion of the mixture substantially devoid of its valuable metal particulate. In one embodiment, electrostatic charging devices are utilized to more efficiently assist the skimming operations within the apparatus.

11 Claims, 6 Drawing Figures

PRECIOUS METAL RECOVERY APPARATUS

BACKGROUND OF THE INVENTION

The present invention relates, in general, to resource recovery and filtering systems and, in particular, to an apparatus for recovering precious metal particles from a liquid mixture environment.

Several industries today, in various occupational areas, are involved with the utilization of precious metal materials in conjunction with various processes. In many of these occupations, such as dentistry and/or the manufacture of jewelry, precious metal scraps are generated in the form of relatively small, as well as microscopic particles of silver, gold, etc., which are often captured in a liquid solution. In the jewelry formation application, the rinsing of newly formed, machined or cast jewelry items or products, creates a liquid mixture containing such precious metal particles. In the field of dentistry, the utilization of silver, gold or alloys containing same in a patients' mouth, creates a liquid mixture of precious metal particles, saliva and discharged water which accumulates in the patient's mouth where the dentist is working. Usually, a dentist's "evacuator" is utilized to remove this liquid mixture wherein the evacuator comprises a specialized vacuum device that literally sucks the mixture from areas of accumulation in the mouth for contaminating disposal of same into general sewer systems.

As of late, especially, as well as throughout history, the precious metals being disposed of are of substantial value so as to make necessary and economically feasible their reclamation. Accordingly, more and more jewelry manufacturers, dentists and others in occupations utilizing precious metals, such as the microcircuit electronics industry, have a desire to somehow recover all of the precious metal particles formerly, though undesirably, discarded.

While several filters exist today, there are often problems inherent with such filters when it comes to recovering precious metal particles ranging in size from microscopic to pebble-sized. Most, if not all, such filters utilize a screen mesh or paper filter media through which the liquid is directed in order to accumulate and save such particles. By the nature of such paper or screen filters, extremely small microscopic particles are still capable of passing therethrough and can be lost, since any attempt to reduce the porosity of the filter often results in undesirable clogging of the unit altogether. Additionally, when some of the precious metal particles are recovered through the use of such filters, it is often difficult to, in turn, separate the recovered precious metal particles from the filtering medium itself for truly effective reclamation.

It is thus an object of the present invention to provide an apparatus for recovering precious metal particles which is relatively easy to install, in dental evacuation systems, for example, which is extremely efficient at recovering otherwise disposed of precious metal particles.

It is also an object of the present invention to provide such an apparatus which is less likely to succumb to clogging and jamming due to its continuous flow design and at the same time is capable of going for substantial periods of time without requiring emptying.

Further, it is an object of the present invention to provide such a precious metal recovery device which is capable of recovering virtually microscopic particles, as well as larger particles of precious metal while at the same time protecting the pump and other components of a particular evacuation system from such rapidly moving and abrasive metal particles, and for keeping such contaminating metal particles out of sewer systems in accordance with State and Federal environmental requirements.

It is also an object of the present invention to provide such a recovery apparatus which readily discloses the level of accumulated particulate at virtually any point of time during its use, one which is relatively inexpensive to fabricate and maintain especially in view of the value imparted by such precious metal reclamation.

These and other objects of the invention will become apparent in light of the present specification.

SUMMARY OF THE INVENTION

The present invention comprises an apparatus for recovering precious metal particles from a liquid mixture environment and includes apparatus enclosure means which define a sealed chamber into which the liquid mixture is directed. Mixture input means at a first end of the chamber directs the liquid mixture into the apparatus enclosure and a plurality of baffled compartment means operably disposed within the chamber and arranged in succession along the longitudinal axis and spanning the width of the enclosure, cooperate with one another to describe a liquid mixture flow path along this longitudinal axis. The baffled compartments include means for jogging and skimming the precious metal particles from the liquid mixture as the mixture flows through the apparatus along the flow path to promote the segregation and settling of the precious metal particles from the liquid mixture to one or more desired regions within the sealed chamber where the liquid mixture "pools" with minimal currents. Flow output means, at a second end of the chamber opposite the first end, direct the segregated liquid now devoid of most, if not all, its precious metal particles, from the sealed chamber for disposal thereof under the flow directed by the pump.

In a preferred embodiment, the apparatus enclosure is substantially rectangular in shape and has one removable side so as to make capable the cleaning, maintenance and removal of the accumulated precious metal particles from within the apparatus. The removable side is substantially parallel to the longitudinal axis of the apparatus enclosure and is removable from its sealed position to an open "emptying" position through the pivotal attachment of the side member along a proximate side of the apparatus. The removable pivotable side is capable of being maintained in its closed position by closure means. Alternatively, the top and sides may be integrally removable from the bottom to more efficiently expose the compartments for removal of recovered particles.

In a preferred embodiment of the invention, also, one or more of the sides of the apparatus itself are of a substantially transparent material, such as lucite or acrylic, so as to enable the viewing of the accumulated particles within the sealed chamber, for purposes of informing the user as to when the apparatus should be emptied of such particles. In an alternative embodiment, the invention includes accumulation signalling means which are capable of signalling the user at a certain level of accumulation, for emptying the apparatus towards reclaiming the precious metal particles. In this preferred embodiment, the accumulation signalling device is electronically operated and capable of being activated upon the presence of a predetermined amount of electrically conductible recovered precious metal.

Preferably, the mixture input and flow output means comprise liquid conduits which increasingly taper outwardly as the respective conduits approach the actual apparatus enclosure. Through such a tapered conduit design, the speed and intensity of the flow of liquid mixture can be reduced within the enclosure to in turn reduce turbulence of the liquid within the enclosure. Excess turbulence is reduced by several structural features of the present invention, since inadvertent or excess turbulence would be capable of reducing the effectiveness and efficiency of the skimming and jogging devices which serve to "filter" the relatively small particles of precious metal from the precious metal-liquid mixture. In an attempt to further reduce the turbulence, the invention contemplates the utilization of a downwardly angled release aperture on the mixture input means which is capable of directing the liquid mixture into a first "initial" one of the plurality of baffled compartments while simultaneously reducing the turbulence of the mixture as it is directed into the liquid mixture flow path.

In the preferred embodiment of the invention, each of the plurality of baffled compartment means comprises a substantially U-shaped particle entrapment region into which the liquid mixture is introduced, an elevated standard under which the liquid mixture passes as it proceeds along the mixture flow path towards the U-shaped particle entrapment of the next succeeding baffled compartment, and skimming standard means over which the fluid mixture gently cascades to further segregate particles of precious metal from the liquid mixture as it flows along the mixture flow path.

In conjunction with these baffled compartments, the invention relies upon jogging means which includes a plurality of jogging fingers which emanate along the flow path for further baffling and restricting the capabilities of the precious metal particles to proceed along the flow path, thus further segregating and settling the particles along to a desired region, usually the floor of the compartments, in the sealed chamber. Other jogging means comprise a plurality of accumulation fins which receive and store particles of precious metal which fall towards the bottom of the baffled compartments and which further reduce the turbulence of the liquid mixture as it proceeds along the liquid mixture flow path.

Skimming elements are also utilized and, in one embodiment, comprise emanating protrusions from elements of the baffled compartment. These elements serve to further skim the liquid mixture to additionally segregate the metal particles therefrom. The skimming means in one embodiment comprises a returning throat portion proximate to the upper region of the U-shaped entrapment member which more effectively accumulates particles within the entrapment region itself. The throat particles turns inwardly to restrict the opening into the U-shaped region and then turns outwardly thereafter to permit renewed flow of the liquid mixture along the flow path.

The "initial" baffled compartment, that is, the baffled compartment most closely proximate to the mixture input means, includes an elevated standard which is integrated with the U-shaped entrapment region. The elevated standard in this particular baffled compartment forms a substantially curved splash plate proximate to the release aperture in the mixture input means so as to direct, with minimal turbulence, the incoming liquid mixture into that first compartment's U-shaped entrapment region. Additionally, this initial compartment is larger in its length dimension than the succeeding baffled compartments for the purpose of accomodating the greater occurence of particle segregation at the beginning of the flow path. In another embodiment of the invention each succeeding baffled compartment is slightly shorter along its length than the immediately preceding compartment so as to most efficiently accommodate the ever decreasing precious metal particle content ratio along the liquid mixture flow path.

Preferably, four baffled compartments are utilized in conjunction with the precious metal recovery apparatus. Additionally, it is preferred that the lower interior dimension of the flow output conduit be substantially equal in elevation to the elevation of the top of each of the skimming standards to more effectively promote close placid skimming of the mixture along the flow path and to preclude giving the opportunity to the mixture to substantially and easily "flow" over the skimming standards. In accordance with this objective, it is preferable that the lower interior dimension of the mixture input be at an elevation substantially higher than the elevation of the tops of the skimming standard (and in turn the lower interior dimension of the flow output) within the baffled compartment so as to produce minimal turbulence while permitting only a reasonably thin mixture of liquid and precious metal to gently cascade over the skimming standards.

The bottom of the initial compartment's entrapment region is elevated higher than the bottoms of successive U-shaped entrapment regions in the baffling compartments further down the mixture flow path. This construction allows the initial compartment to accumulate out substantially larger portions of segregated particles while not blocking the mixture flow path and to further reduce turbulence that could be created within the sealed chamber by blockage and the natural tendency of mixture to "shoot" through and/or around such blockage.

One embodiment of the invention calls for the utilization of electrical charging means which imposes a first electrical ion charge on the mixture as it enters the apparatus while imposing a second, opposite electrical charge on the mixture while it is passing through one or more of the baffled compartments, to electrically attract the precious metal particles to desired accumulation regions.

Additionally, it is preferable that, the pump means be interposed within or after the position of the flow output means so as to effectively interpose the recovery apparatus before the precious metal particles flow through the pump, to protect the components of the pump itself.

Further, in an effort to minimize the turbulence while maximizing the effective skimming action of the apparatus, the invention contemplates the utilization of an apparatus enclosure which is substantially three times the diameter of the mixture input means, proximate to the position where the liquid mixture enters the apparatus enclosure.

DETAILED DESCRIPTION OF THE DRAWINGS

Figure 1:
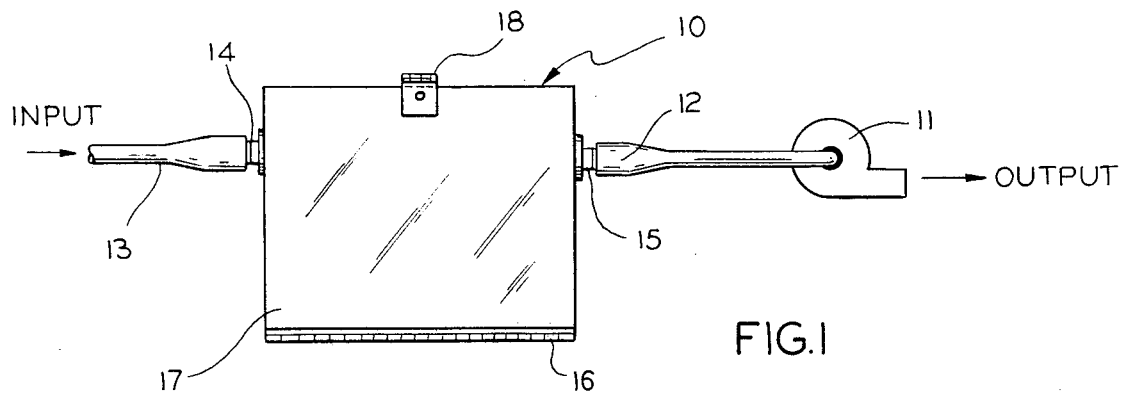
FIG. 1 of the drawings is a front elevational view of the precious metal recovery apparatus showing particularly the removable side of the apparatus, as well as the mixture input and flow output means connected thereto.

While this invention is susceptible of embodiment in many different forms, there is shown in the drawings and will herein be described in detail, several specific embodiments, with the understanding that the present disclosure is to considered as an exemplification of the principles of the invention and is not intended to limit the invention to the embodiments illustrated.

Precious metal recovery apparatus 10 is shown in FIG. 1 as including mixture input means 13-14, as well as flow output means 12-15. Substantially transparent side 17 is hinged at hinge 16 to apparatus 10 so as to be pivotable between an open "emptying" position and a closed secured position, wherein it is maintained in place by side closure means 18 as shown in FIG. 1. Pump 11 is interposed into flow output means 12-15 for initially imparting and directing flow of the liquid mixture, which continues to flow by gravity into mixture input means 13-14, through the apparatus enclosure of apparatus 10 and out the flow output conduit 12-15.

Figure 2:
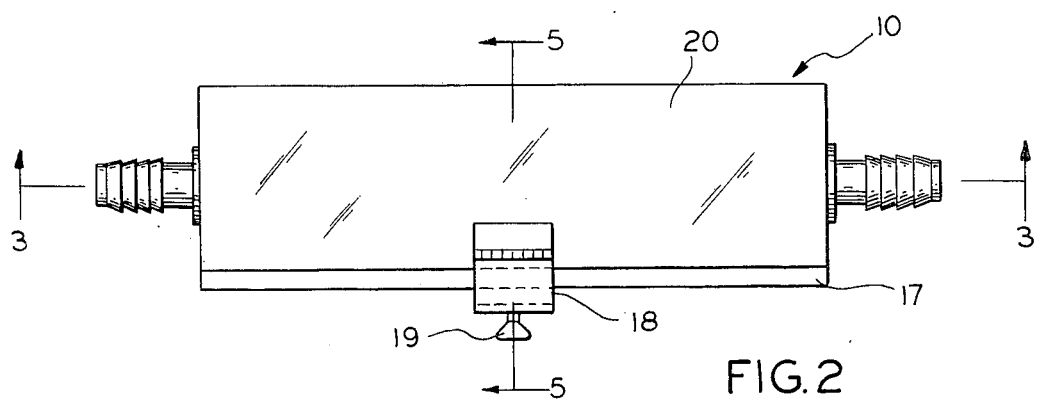
FIG. 2 of the drawings is a top view of the recovery apparatus.

Top side 20, as well as the edge of pivoting side 17 are shown in FIG. 2. Also shown, is side closure means 18 with fastener 19 utilized to retain side 17 in place against the rest of apparatus 10 while the device is utilized in the precious-metal recovery operation.

Figure 3:
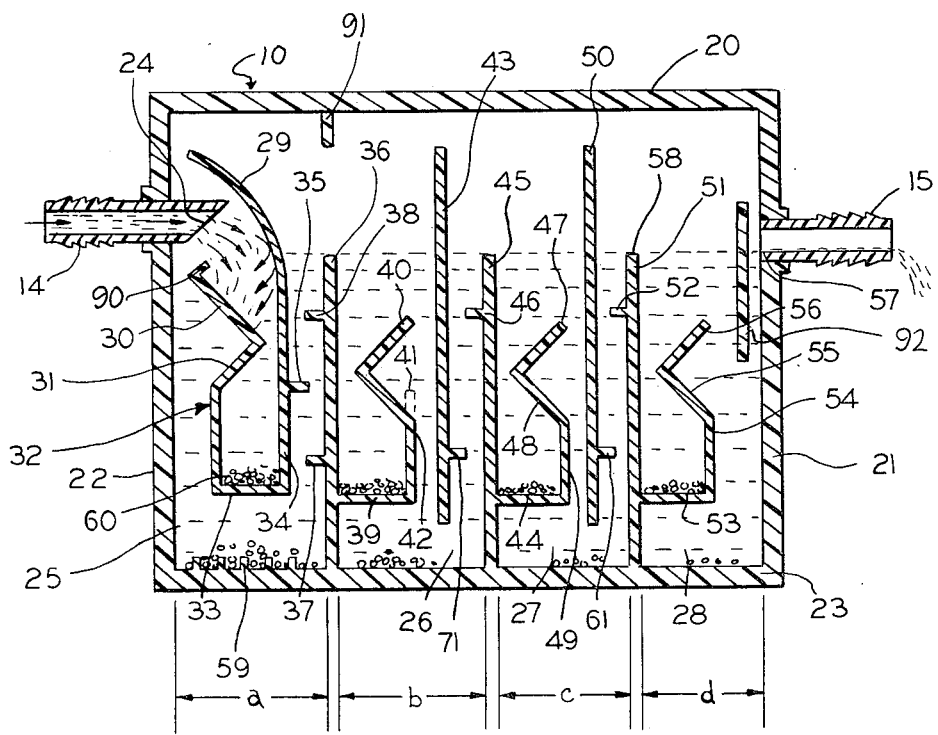
FIG. 3 is a front cross-sectional view of the apparatus taken along lines 3—3 of FIG. 2 and looking in the direction of the arrows, showing particularly the apparatus enclosure together with the baffled compartments therewithin.

Apparatus 10 is shown in FIG. 3 as including mixture input means 14 with downwardly slanted release aperture 24. In the previously discussed dental "evacuation" application of the apparatus, the liquid mixture includes water, saliva and other debris from a patient's mouth, and further includes precious metals such as silver and gold in particle form. As this liquid mixture is released at release aperture 24, it flows between splash plate 29 on elevated member 34 which is integrated with U-shaped entrapment region 32. The liquid mixture passes inwardly turned throat portion 31 at the top of U-shaped region 32 and begins to fill region 32 while at the same time permitting some of the precious metal embodied in the liquid mixture to form as sediment 60 on top of bottom 33 of U-shaped portion 32. The mixture containing the rest of the above-described liquid and solid mixture then flows over the top of outwardly turned throat portion 30 and jogging member 90, and drops to the bottom of the first "initial" compartment 25 where the entire mixture is exposed to a series of accumulation fins such as accumulation fin 59. Even more particulate is accumulated at that point. Element 91 precludes inadvertent splashing or arcing of the liquid mixture into the next compartment along the flow path.

The liquid mixture continues to flow by pump 11 of FIG. 1 and gravity, past jogging fingers 37, 35 and 38, respectively. These jogging fingers serve to additionally baffle and skim the mixture as it elevates to the height of the top of skimming standard 36. As the mixture elevates to that height, it gently cascades over skimming standard 36 to skim yet further particulate from the mixture as it proceeds into the second chamber of the apparatus.

In equivalent fashion, the mixture then cascades into the U-shaped entrapment region in the second compartment 26. In so doing, it cascades over skimming member 36 onto floor 39 of the entrapment region and elevates past its inwardly turned throat, as well as its outwardly turned throat portion 40, after which it flows to the bottom of the second compartment 26. As the mixture fills compartment 26 it is additionally skimmed by vertical skimming elements such as skimming element 41. The mixture with its ever-decreasing ratio of remaining precious-metal particles then passes under elevated standard 43 having jogging finger 71 free for yet further skimming.

The mixture flows over skimming standard 45 with jogging finger 46 into the bottom 44 of the entrapment region of compartment 27 and eventually into the bottom of compartment 27. This mixture flows under elevated standard 50 with jogging member 61 until it cascades over skimming element 51, at end 58, for entry into the fourth compartment 28. Elevated standard 92 precludes the creation of turbulence proximate to the output where gravity and suction carry off the remaining solution.

Release of this virtually metal particle-free solution occurs at release aperture 57 of flow output conduit 15 which, by itself, serves to additionally skim the remaining vestiges of precious metal particles from the release mixture. At conduit 15, gravity-flow assisted by vacuum pressure of pump 11 directs the solution on.

In the preferred embodiment, dimension "a" of compartment 25 is larger than dimension "b" adjacent compartment 26 which is, in turn, larger than dimension "c" of adjacent compartment 27, and so on, since the degree of segregation of particulate decreases as the mixture flows along the flow mixture path through the successive compartments. It should also be noted that, in the preferred embodiment, the interior elevation of release aperture 57, in flow output conduit 15, is at a substantially equivalent elevation as the tops of skimming standards 36, 45 and 51, while the mixture input means 14, at its release aperture 24, has a lower interior dimension substantially higher than the levels of the skimming standards, as well as higher than the level of the release aperture in flow output conduit 15. Additionally, the height of floor 33 of U-shaped entrapment region 32 in initial compartment 25 is substantially higher than floors 39, 44 and 53 in the other compartments to accommodate the greater degree of accumulation and segregation occurring in the initial compartment without creating excessive turbulence.

Figure 4:
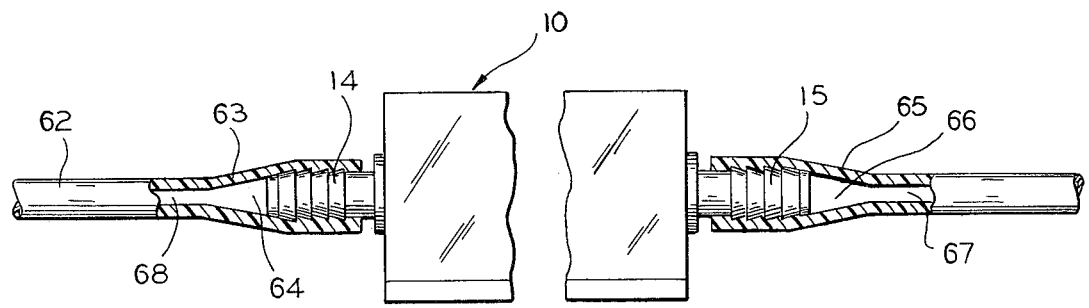
FIG. 4 of the drawings is a partial cross-sectional view of the mixture input and flow output means of the apparatus.

Excessive turbulence is also reduced, not only by the plurality of skimming and jogging means as shown in FIG. 3, but also by the utilization of increasingly tapered mixture input means 62 and flow output means 65 as shown in FIG. 4. In such an arrangement the interior dimension of mixture input means 62 increases from its size at portion 68 to a larger outwardly tapered side at 64 before it is even connected at conduit connection device 14 proximate to apparatus 10. In like fashion, conduit 65 tapers outwardly from region 67 to region 66 where it is connected by conduit connection conduit 15 proximate to apparatus 10.

Figure 5:
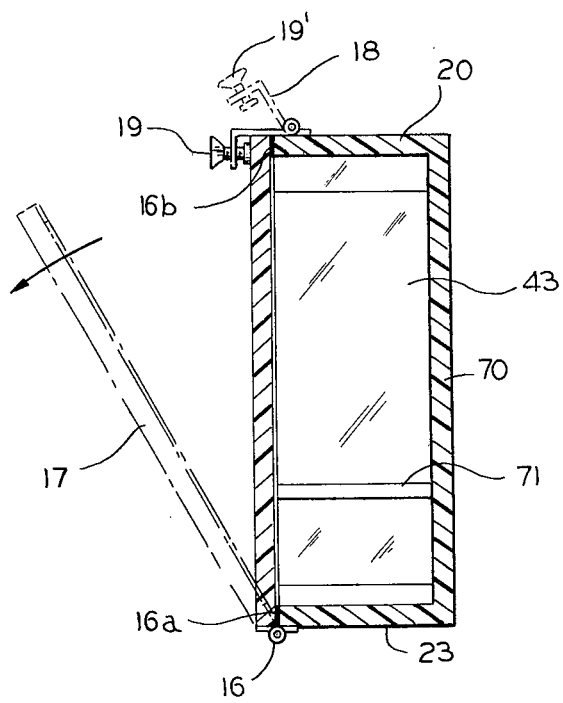
FIG. 5 of the drawings is a cross-sectional elevated side view taken along lines 5—5 of FIG. 2 and looking in the direction of the arrows.

Side 17 is shown being pivoted to its open position in FIG. 5 through its pivoted connection at hinge 16. Also shown in FIG. 5 are seals 16a and 16b, side closure means 18 with attachment fastener 19, as well as jogging finger 71, spanning the entire width of the chamber as attached to elevated standard 43.

Figure 6:
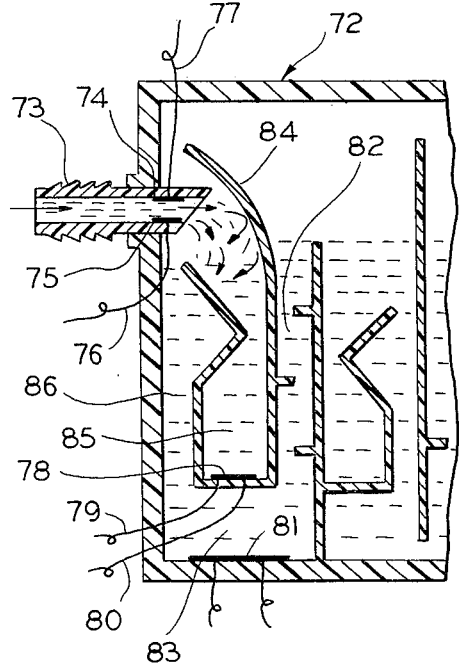
FIG. 6 is a partial cross-sectional view of the apparatus showing particularly the mixture input means and initial baffled compartment together with electrical charging means.

In FIG. 6, another embodiment of the apparatus is shown in which electrical charging means 74-75 are interposed in the mixture input means 73 for the purpose of imposing a particular ion charge on the mixture entering apparatus 72. Elsewhere within the initial compartment 83, for example, are electrical charging means 78 and 81 which are capable of imposing an opposite electrical charge on the accumulated mixture therein for the purpose of more effectively precipitating out the oppositely charged particles within the mixture. In such a manner, particles would then accumulate on plates 78 and 81 by way of electrostatic attration.

The foregoing description and drawings merely explain and illustrate the invention and the invention is not limited thereto, except insofar as the appended claims are so limited, as those skilled in the art who have the disclosure before them will be able to make modifications and variations therein without departing from the scope of the invention.

What is claimed is:

1. An apparatus for recovering precious metal particles from a liquid mixture environment in a vacuum evacuation system, said apparatus comprising:
   apparatus enclosure means defining a sealed chamber into which said liquid mixture flows together with air;
   mixture input means at a first end of said chamber for directing said liquid mixture into said apparatus enclosure means;
   a plurality of baffled compartment means operably disposed within said sealed chamber arranged in succession along the longitudinal axis of said apparatus enclosure means;
   each of said plurality of baffled compartment means spanning the width of said enclosure means and cooperating with one another to describe a liquid mixture flow path along said longitudinal axis;
   each of said plurality of baffled compartment means further including means for jogging and skimming said precious metal particles from said liquid mixture as said mixture flows through said apparatus along said flow path to promote the segregation and settling of said particles from said liquid to one or more desired regions within said sealed chamber;
   said mixture flowing through said baffled compartment means by gravity flow along said flow path, independent of the flow of said air above said mixture flow path;
   flow output means at a second end of said chamber opposite said first end for directing segregated liquid, devoid of its precious metal particles, from said sealed chamber for disposal thereof as directed by said vacuum in said evacuation system;
   said air flowing directly between said mixture input and flow output means separate from the flow path for said mixture, as prompted by said evacuation system vacuum;
   one or more of said plurality of baffle compartment means comprising a substantially U-shaped particle entrapment region into which said liquid mixture is introduced,
   an elevated standard under which said liquid mixture passes as it proceeds along said mixture flow path towards the U-shaped particle entrapment area of the next succeeding compartment, and
   skimming standard means over which said fluid mixture cascades to further ferret and segregate said particles of precious metal from said liquid mixture as it flows along said mixture flow path.

2. The invention according to claim 1 in which the baffled compartment most closely proximate to said mixture input means includes an elevated standard integrated with said U-shaped entrapment region,
   said elevated standard forming a substantially curved splash plate proximate to a release aperture in said mixture input means so as to direct, with a minimal turbulence, incoming liquid mixture into said U-shaped entrapment region.

3. The invention according to claim 2 in which said initial compartment most closely proximate to said mixture input means comprises an initial compartment which is larger in length than one or more of said succeeding baffled compartments for purpose of accommodating a greater occurrence of particle segregation and accumulation.

4. The invention according to claim 3 in which succeeding baffled compartments after said initial compartment are increasingly slightly smaller in dimension to most efficiently accommodate the ever-decreasing precious metal particle content ratio along said liquid mixture flow path.

5. The invention according to claim 1 in which four baffled compartments describe the flow path through said apparatus enclosure means.

6. The invention according to claim 1 in which the lower interior dimension of said flow output means is substantially equal in elevation to the elevation of the top of each of said skimming standards within respective baffled compartments.

7. The invention according to claim 6 in which the lower interior dimension of said mixture input means is at an elevation substantially higher than the elevation of the tops of said skimming standards within said plurality of baffled compartment means.

8. An apparatus for recovering precious metal particles from a liquid mixture environment in a vacuum evacuation system, said apparatus comprising:
   apparatus enclosure means defining a sealed chamber into which said liquid mixture flows together with air;
   mixture input means at a first end of said chamber for directing said liquid mixture into said apparatus enclosure means;
   a plurality of baffled compartment means operably disposed within said sealed chamber arranged in succession along the longitudinal axis of said apparatus enclosure means;
   each of said plurality of baffled compartment means spanning the width of said enclosure means and cooperating with one another to describe a liquid mixture flow path along said longitudinal axis;
   each of said plurality of baffled compartment means further including means for jogging and skimming said precious metal particles from said liquid mixture as said mixture flows through said apparatus along said flow path to promote the segregation and settling of said particles from said liquid to one or more desired regions within said sealed chamber;

said mixture flowing through said baffled compartment means by gravity flow along said flow path, independent of the flow of said air above said mixture flow path;

flow output means at a second end of said chamber opposite said first end for directing segregated liquid, devoid of its precious metal particles, from said sealed chamber for disposal thereof as directed by said vacuum in said evacuation system;

said air flowing directly between said mixture input and flow output means separate from the flow path for said mixture, as prompted by said evacuation system vacuum; and electrical charging means for imposing a first electrical charge on said liquid mixture as it enters said apparatus and which imposes a second opposite electrical charge in said sealed chamber to electrically attract said precious metal particles therewithin so as to further segregate them from said liquid mixture as it flows along said liquid mixture flow path.

9. An apparatus for recovering precious metal particles from a liquid mixture environment in a vacuum evacuation system, said apparatus comprising:

apparatus enclosure means defining a sealed chamber into which said liquid mixture flows;

mixture input means at a first end of said chamber for directing said mixture into said apparatus enclosure means;

a plurality of baffled compartment means operably disposed within said sealed chamber arranged in succession along the longitudinal axis of said apparatus enclosure means;

each of said plurality of baffled compartment means spanning the width of said enclosure means and cooperating with one another to describe a liquid mixture flow path along said longitudinal axis;

each of said plurality of baffled compartments means further including means for jogging and skimming said precious metal particles from said liquid mixture as said mixture flows through said apparatus along said flow path to promote the segregation and settling of said particles from said liquid to one or more desired regions within said sealed chamber;

flow output means at a second end of said chamber opposite said first end for directing segregated liquid, devoid of its precious metal particles from said sealed chamber for disposal thereof as directed by said vacuum in said evacuation system;

accumulation signaling means which are capable of signaling a user of said apparatus, upon accumulation of precious metal particles to a desired amount, of the need for emptying said apparatus for removal and reclamation of said precious metal particles; and said accumulation signaling means comprising an electronically operated signaling device capable of being activated upon the presence of a predetermined amount of electricity conductable recovered precious metal.

10. An apparatus for recovering precious metal particles from a liquid mixture environment in a vacuum evacuation system, said apparatus comprising:

apparatus enclosure means defining a sealed chamber into which said liquid mixture flows;

mixture input means at a first end of said chamber for directing said liquid mixture into said apparatus enclosure means;

a plurality of baffled compartment means operably disposed within said sealed chamber arranged in succession along the longitudinal axis of said apparatus enclosure means;

each of said plurality of baffled compartment means spanning the width of said enclosure means and cooperating with one another to describe a liquid mixture flow path along said longitudinal axis;

each of said plurality of baffled compartment means further including means for jogging and skimming said precious metal particles from said liquid mixture as said mixture flows through said apparatus along said flow path to promote the segregation and settling of said particles from said liquid to one or more desired regions within said sealed chamber;

flow output means at a second end of said chamber opposite said first end for directing segregated liquid, devoid of its precious metal particles from said sealed chamber for disposal thereof as directed by said vacuum in said evacuation system;

one or more of said plurality of baffle compartment means comprising a substantially U-shaped particle entrapment region into which said liquid mixture is introduced;

an elevated standard under which said liquid mixture passes as it proceeds along said mixture flow path towards the U-shaped particle entrapment area of the next succeeding compartment;

skimming standard means over which said fluid mixture cascades to further ferret and segregate said particles of precious metal from said liquid mixture as it flows along said mixture flow path;

said skimming means further including a returning throat portion proximate to the upper portion of one or more of said U-shaped entrapment regions for more effectively accumulating particles within the entrapment region itself;

said throat returning inwardly to restrict the opening into said U-shaped region and turning outwardly thereafter to permit renewed flow of said liquid mixture along said flow path.

11. An apparatus for recovering precious metal particles from a liquid environment in a vacuum evacuation system, said apparatus comprising:

apparatus enclosure means defining a sealed chamber into which said liquid mixture flows;

mixture input means at a first end of said chamber for directing said liquid mixture into said apparatus enclosure means, a plurality of baffled compartment means operably disposed within said sealed chamber arranged in succession along the longitudinal axis of said apparatus enclosure means;

each of said plurality of baffled compartment means spanning the width of said enclosure means and cooperating with one another to describe a liquid mixture flow path along said longitudinal axis;

each of said plurality of baffled compartment means further including means for jogging and skimming said precious metal particles from said liquid mixture as said mixture flows through said apparatus along said flow path to promote the segregation and settling of said particles from said liquid to one or more desired regions within said sealed chamber;

flow output means at a second end of said chamber opposite said first end for directing segregated liquid, devoid of its precious metal particles from said sealed chamber for disposal thereof as directed by said vacuum in said evacuation system;

one or more of said plurality of baffled compartment means comprising a substantially U-shaped particle entrapment region into which said liquid mixture is introduced;

an elevated standard under which said liquid mixture passes as it proceeds along said mixture flow path towards the U-shaped particle entrapment area of the next succeeding compartment;

skimming standard means over which said fluid mixture cascades to further ferret and segregate said particles of precious metal from said liquid mixture as it flows along said mixture flow path;

the baffled compartment most closely proximate to said mixture input means including an elevated standard integrated with said U-shaped entrapment region;

said elevated standard forming a substantially curved splash plate proximate to a release aperture in said mixture input means so as to direct, with minimal turbulence, incoming liquid mixture into said U-shaped entrapment region;

said initial compartment most closely proximate to said mixture input means comprising an initial compartment which is larger in length than one or more of said succeeding baffled compartments for purpose of accommodating a greater occurrence of particle segregation and accumulation; and the bottom of said U-shaped entrapment region in said initial baffle compartment being elevated higher than the bottoms of successive U-shaped entrapment region in said successive baffling compartment means.

* * * * *

UNITED STATES PATENT AND TRADEMARK OFFICE
CERTIFICATE OF CORRECTION

PATENT NO. : 4,326,952
DATED : April 27, 1982
INVENTOR(S) : Gene J. Blake

It is certified that error appears in the above-identified patent and that said Letters Patent are hereby corrected as shown below:

Col. 3, line 60           "particles" should be instead
                                       --portion--

Signed and Sealed this

Sixth Day of July 1982

[SEAL]

Attest:

GERALD J. MOSSINGHOFF

Attesting Officer       Commissioner of Patents and Trademarks